US011332704B2

(12) United States Patent
Tajima et al.

(10) Patent No.: US 11,332,704 B2
(45) Date of Patent: May 17, 2022

(54) CULTURE DEVICE, CULTURE SYSTEM, AND CULTURE METHOD

(71) Applicant: UNIVERSAL BIO RESEARCH CO., LTD., Matsudo (JP)

(72) Inventors: Hideji Tajima, Chiba (JP); Tetsuya Ueda, Chiba (JP)

(73) Assignee: UNIVERSAL BIO RESEARCH CO., LTD., Chiba (JP)

(*) Notice: Subject to any disclaimer, the term of this patent is extended or adjusted under 35 U.S.C. 154(b) by 310 days.

(21) Appl. No.: 14/903,195

(22) PCT Filed: Jul. 8, 2014

(86) PCT No.: PCT/JP2014/068103
§ 371 (c)(1),
(2) Date: Jan. 6, 2016

(87) PCT Pub. No.: WO2015/005299
PCT Pub. Date: Jan. 15, 2015

(65) Prior Publication Data
US 2016/0137967 A1    May 19, 2016

(30) Foreign Application Priority Data
Jul. 9, 2013  (JP) .............................. JP2013-143800

(51) Int. Cl.
*C12M 1/12* (2006.01)
*C12M 3/06* (2006.01)
(Continued)

(52) U.S. Cl.
CPC ............ *C12M 35/06* (2013.01); *C12M 23/04* (2013.01); *C12M 25/16* (2013.01); *C12M 27/16* (2013.01);
(Continued)

(58) Field of Classification Search
CPC ................ G02B 1/111; G02B 27/0006; Y10T 428/24967; Y10T 428/265; Y10T 428/266;
(Continued)

(56) References Cited

U.S. PATENT DOCUMENTS 5,536,475 A * 7/1996 Moubayed ............. A61K 35/16
209/217
2004/0248291 A1 12/2004 Yamamoto et al.
(Continued)

FOREIGN PATENT DOCUMENTS

EP    1260583 A1   11/2002
JP    H05-317046 A  12/1993
(Continued)

OTHER PUBLICATIONS

Extended European Search Report dated Jan. 9, 2017 in corresponding EP Patent Application No. 14823551.8.
(Continued)

*Primary Examiner* — Lydia Edwards

(57) ABSTRACT

This culture device comprises: a culture container which houses cells, magnetic particles and a culture medium; a temperature adjustment unit for adjusting the temperature of the culture container; a magnet which is provided to the outside of the culture container; a magnetic force adjustment unit for adjusting the magnetic force of the magnet; and a control unit for controlling the operation of the magnetic force adjustment unit. The magnetic force adjustment unit adjusts the magnetic force of the magnet, thereby holding magnetic particles and cells in a predetermined region within the culture container, or dispersing the magnetic particles and cells within the culture container.

25 Claims, 8 Drawing Sheets

(51) Int. Cl.
  *C12M 1/26* (2006.01)
  *C12M 1/42* (2006.01)
  *C12M 1/34* (2006.01)
  *C12M 1/00* (2006.01)
  *C12N 13/00* (2006.01)

(52) U.S. Cl.
  CPC ............ *C12M 33/00* (2013.01); *C12M 41/00* (2013.01); *C12M 41/14* (2013.01); *C12N 13/00* (2013.01)

(58) Field of Classification Search
  CPC ..... Y10T 428/31507; Y10T 428/31612; Y10T 428/31663; Y10T 428/31667; C12M 23/04; C12M 25/16; C12M 27/16; C12M 33/00
  See application file for complete search history.

(56) References Cited

U.S. PATENT DOCUMENTS

| | | | |
|---|---|---|---|
| 2010/0009335 A1* | 1/2010 | Joseph | .................. C12M 41/44 435/3 |
| 2011/0127222 A1* | 6/2011 | Chang-Yen | ............ C12M 47/04 210/695 |
| 2011/0198286 A1* | 8/2011 | Niazi | .................... C12M 23/14 210/638 |
| 2014/0147015 A1 | 5/2014 | Bajema et al. | |

FOREIGN PATENT DOCUMENTS

| | | |
|---|---|---|
| JP | 2004-520028 A | 7/2004 |
| JP | 2004-254519 A | 9/2004 |
| JP | 2004-313008 A | 11/2004 |
| JP | 2005-312386 A | 11/2005 |
| WO | WO-02-051985 A2 | 7/2002 |
| WO | WO2009/117611 A2 | 9/2009 |

OTHER PUBLICATIONS

International Search Report and Written Opinion of the ISA for PCT/JP2014/068103, ISA/JP, dated Oct. 21, 2014.

Yukie Naka et al., "Neurite Outgrowths of Neurons Using Neurotrophin-Coated Nanoscale Magnetic Beads", Journal of the Society for Bioscience and Bioengineering, Japan, Feb. 25, 2006 (Feb. 25, 2006), 84(2), p. 71, with partial English translation.

* cited by examiner (A) Day 0

(B) Day 3

(C) Day 5

CULTURE DEVICE, CULTURE SYSTEM, AND CULTURE METHOD

CROSS REFERENCE TO RELATED APPLICATIONS

This application is a 371 U.S. National Stage of International Application No. PCT/JP2014/068103, filed Jul. 8, 2014, which claims the benefit of Japanese Patent Application No. 2013-143800, filed Jul. 9, 2013. The entire disclosures of the above applications are incorporated herein by reference.

TECHNICAL FIELD

The present invention relates to a culture device, a culture system and a culture method for performing cell culture using magnetic particles.

BACKGROUND ART

Adherent cells such as somatic cells adhere to the bottom surface of a culture vessel and form a foothold before repeating cell division and cell elongation to increase the number thereof. In this regard, if the increase in the cell number keeps going on, the cells start to scramble for adhesion area on the bottom surface of the vessel since the cells remain adhered to the bottom surface of the culture vessel. Therefore, if the increase in the cell number continues, there will be no space between the cells and eventually the cells will be multi-layered, due to which the cells will suffocate without sufficient nutrients (confluent condition) and result in dead cells.

Accordingly, when adherent cells are cultured in a culture vessel, the cells need to be cultured while detaching them from the culture vessel and transferring them to other vessel at a given cell number (given density) before reaching the confluent condition so as to keep sufficient nutrients to go throughout the cells (subculture).

In order to detach the cells from the culture vessel and transfer them into other vessel, there is a need to use an enzyme solution such as trypsin to degrade the cell adhesion protein to allow the cells to float or use a scraper to physically detach the cells from the culture vessel. In the field of cell culture, it is well known that these methods are unfavorable treatments since they will place stress on the cells. For example, trypsin is known to be toxic to cells and it is known that a trypsin treatment will change the property of the cells and result dead cells. Therefore, it is desirable to minimize such treatments as much as possible that will place stress on cells.

The operation of detaching cells from a culture vessel and transferring them into other vessel is manually conducted in a clean bench. Manual operations are constantly at a risk of contamination.

In view of the above-described problems, in order to culture adherent cells such as somatic cells in a culture vessel, a culture device that is capable of changing the position of the cells is desired so that the cells can stably absorb the nutrients by a completely automated procedure without any manual operation.

Before now, cell cultures that utilize magnetic particles have been known where the cells are attached to the magnetic particles, and then a magnetic field is applied to a culture solution containing the magnetic particles to allow the magnetic particles in the culture solution to move, thereby culturing the cells in a three-dimensional configuration while agitating the magnetic particles (see Patent Document 1), and where the intensity of a magnetic field applied to cell-attached magnetic particles are changed to cause mechanical stress on the cells, thereby culturing the cells (see Patent Document 2). Moreover, these patent documents also describe that the magnet for applying the magnetic field can be moved.

PRIOR ART DOCUMENTS

Patent Documents

Patent Document 1: Japanese Unexamined Patent Application Publication No. 2004-313008
Patent Document 2: Japanese Unexamined Patent Application Publication (translation of PCT) No. 2004-520028

SUMMARY OF THE INVENTION

Problems to be Solved by the Invention

Patent Documents 1 and 2, however, do not describe about retaining (fixing) the cells to a predetermined region or dispersing the cells by using magnetic particles with an external magnet. In particular, the invention of Patent Document 1 conducts culture while agitating cells in a culture solution using a magnetic field of a magnet. Although it uses the magnetic field of the magnet for cell culture, it does not use the magnetic field for agitating the cell, and neither describes nor suggests to culture the cells while retaining them to a predetermined region in the culture vessel.

The objective of the present invention is to provide a novel culture device and culture system with good culture efficiency. Another objective of the present invention is to provide a culture device and a culture system that allow cell culture while retaining the cells to a predetermined region in a culture vessel using a magnetic field of a magnet, wherein the cells are displaceable to a certain extent in the predetermined region.

Furthermore, there has also been a problem in subculturing cells in that the cells need to be moved to another position so as to provide the cells with new environment where they can absorb nutrients, for example, by transferring them to other vessel by manual operation that is associated with a risk of contamination and that places stress on the cells.

In order to solve the above-described problem, another objective of the present invention is to provide a culture device and culture system capable of controlling the position of the cells in a non-contact manner so that the cells can absorb nutrients without manual operation and without placing stress on the cells.

Means for Solving the Problems

In order to solve the above-described problem, the present inventors have gone through keen examination, as a result of which succeeded in controlling the position of cells in a non-contact manner where magnetic particles and the cells are retained to a predetermined region in a culture vessel or the cells are dispersed in the culture vessel by altering the distance between and/or the positions of the culture vessel and a magnet unit placed outside of the culture vessel, thereby accomplishing the present invention.

Thus, the present invention is as follows.
(Item 1) A culture device, comprising: a culture vessel for accommodating cells, magnetic particles that directly or indirectly attach to the cells and a solution; a temperature regulating unit for the culture vessel; a magnet disposed outside the culture vessel; and a magnetic force regulating unit for regulating the magnetic force of the magnet, wherein the magnetic force regulating unit regulates the magnetic force of the magnet to conduct cell culture in a state where the magnetic particles and the cells are retained to a predetermined region in the culture vessel.

(Item 2) The culture device according to (Item 1), wherein the magnetic force regulating unit regulates the magnetic force of the magnet to disperse the magnetic particles and the cells in the culture vessel. (Item 3) The culture device according to (Item 1) or (Item 2), wherein the magnet is a plurality of magnets spaced at intervals. (Item 4) The culture device according to (Item 3), wherein each of the plurality of magnets is arranged so as to oppose one surface of the culture vessel. (Item 5) The culture device according to (Item 3) or (Item 4), wherein each of the plurality of magnets is arranged such that the polarity thereof differs from the polarity of the adjacent magnet. (Item 6) The culture device according to any one of (Item 3) to (Item 5), wherein the plurality of magnets are arranged in a matrix. (Item 7) The culture device according to any one of (Item 1) to (Item 6), wherein the magnetic particles and the cells are condensed or aggregated in a state where they are retained to the predetermined region in the culture vessel. (Item 8) The culture device according to any one of (1) to (7), wherein the magnetic force regulating unit alters the distance between and/or the position of the magnet and the culture vessel.

(Item 9) The culture device according to any one of (Item 1) to (Item 8), wherein the magnetic force regulating unit brings the magnet closer to the culture vessel to conduct cell culture in a state where the magnetic particles and the cells are retained to the predetermined region. (Item 10) The culture device according to any one of (Item 1) to (Item 9), comprising a sliding mechanism for sliding the magnet and the culture vessel relatively with respect to one another. (Item 11) The culture device according to (Item 10), wherein the cell culture is conducted by shake culture with the sliding mechanism. (Item 12) The culture device according to any one of (Item 1) to (Item 11), comprising an oscillating mechanism for oscillating the culture vessel.

(Item 13) The culture device according to any one of (Item 1) to (Item 12), wherein the magnetic force regulating unit charges the solution into the culture vessel or discharges the solution from the culture vessel in a state where the magnetic particles and the cells are retained to the predetermined region in the culture vessel. (Item 14) The culture device according to any one of (Item 1) to (Item 13), wherein the magnetic force regulating unit conducts cell culture by combining multiple movements selected from: bringing the magnet closer; vibrating the magnet; and separating the magnet.

(Item 15) The culture device according to any one of (Item 1) to (Item 14), wherein the magnetic force regulating unit collects the solution containing the cultured cells from the culture vessel in a state where the magnetic particles and the cells can be dispersed in the culture vessel. (Item 16) The culture device according to any one of (Item 1) to (Item 15), wherein at least one of the temperature regulating unit and the magnetic force regulating unit is detachable from the culture vessel. (Item 17) The culture system comprising the culture device according to any one of (Item 1) to (Item 16), the system comprising a supplying section for supplying a material and a solution used for the cell culture to the culture vessel and a magnetic particle separating unit for separating the magnetic particles from the solution containing the cells cultured in the culture vessel.

(Item 18) The culture system according to (Item 17), wherein the solution is transferred by gravity fall. (Item 19) The culture system according to (Item 17) or (Item 18), wherein the supplying section, the culture vessel and the magnetic body separating unit are disposed from top to bottom in this order. (Item 20) The culture system according to any one of (Item 17) to (Item 19), wherein the supplying section and the culture vessel, and the culture vessel and the magnetic body separating unit are connected via pipelines, respectively. (Item 21) The culture system according to (Item 20), comprising valves for opening and closing the respective pipelines. (Item 22) The culture system according to any one of (Item 17) to (Item 21), comprising a dispensing mechanism for dispensing the material and the solution used for cell culture into the supplying section.

(Item 23) A method for culturing a cell, comprising a step of conducting cell culture using the culture device according to any one of (Item 1) to (Item 16). (Item 24) A method for culturing a cell using the culture system according to any one of (Item 17) to (Item 22), the method comprising the steps of: supplying a material and a solution used for cell culture from the supplying section to the culture vessel; culturing cells using the culture device; separating the magnetic particles from the solution containing the cells using the magnetic particle separating unit; and sorting out the cells from the solution separated from the magnetic particles. (Item 25) The method according to (Item 24), comprising a step of dispensing the material or the solution used for cell culture into the supplying section by using the dispensing mechanism. (Item 26) The method according to (Item 24) or (Item 25), wherein a controller automatically performs each of the steps.

Effect of the Invention

According to the present invention, cell culture can be conducted by automatically controlling the position of the cells to allow the cells to absorb nutrients without any manual operation and without placing stress on cells

MODES FOR CARRYING OUT THE INVENTION

Summary

The present invention is a culture device that is capable of automatically controlling the position of cells without any manual operation and without placing stress on the cells, by bringing a magnet provided outside a culture vessel closer to the culture vessel to conduct cell culture in a state where magnetic particles and cells are fixed (retained) on an inner surface (a predetermined region) of the culture vessel, by vibrating the magnet that is close to the culture vessel to shake the magnetic particles and the cells fixed on the inner surface of the culture vessel, and by separating the magnet from the culture vessel to disperse the magnetic particles and the cells in the culture vessel. In addition, the present invention is a cell culture system that is capable of conducting seeding to recovery of the cells in a sterile state in an automatic manner without placing stress to the cells by transferring the solution into the culture device or transferring the solution from the culture device to outside by gravity fall.

Hereinafter, preferable embodiments of the present invention will be described with reference to the drawings. In each of the embodiments, like numerals refer to like parts and the description thereof is omitted. Hereinafter, the term "fix" means to retain magnetic particles and cells to a predetermined region where the magnetic particles and the cells retained to the predetermined region can oscillate to a certain extent.

First Embodiment

A culture device 10 according to a first embodiment of the present invention will be described with reference to FIG. 1. The culture device 10 is provided with a culture vessel 3, a temperature regulating unit 5 and a magnetic force regulating unit 7.

Figure 1:
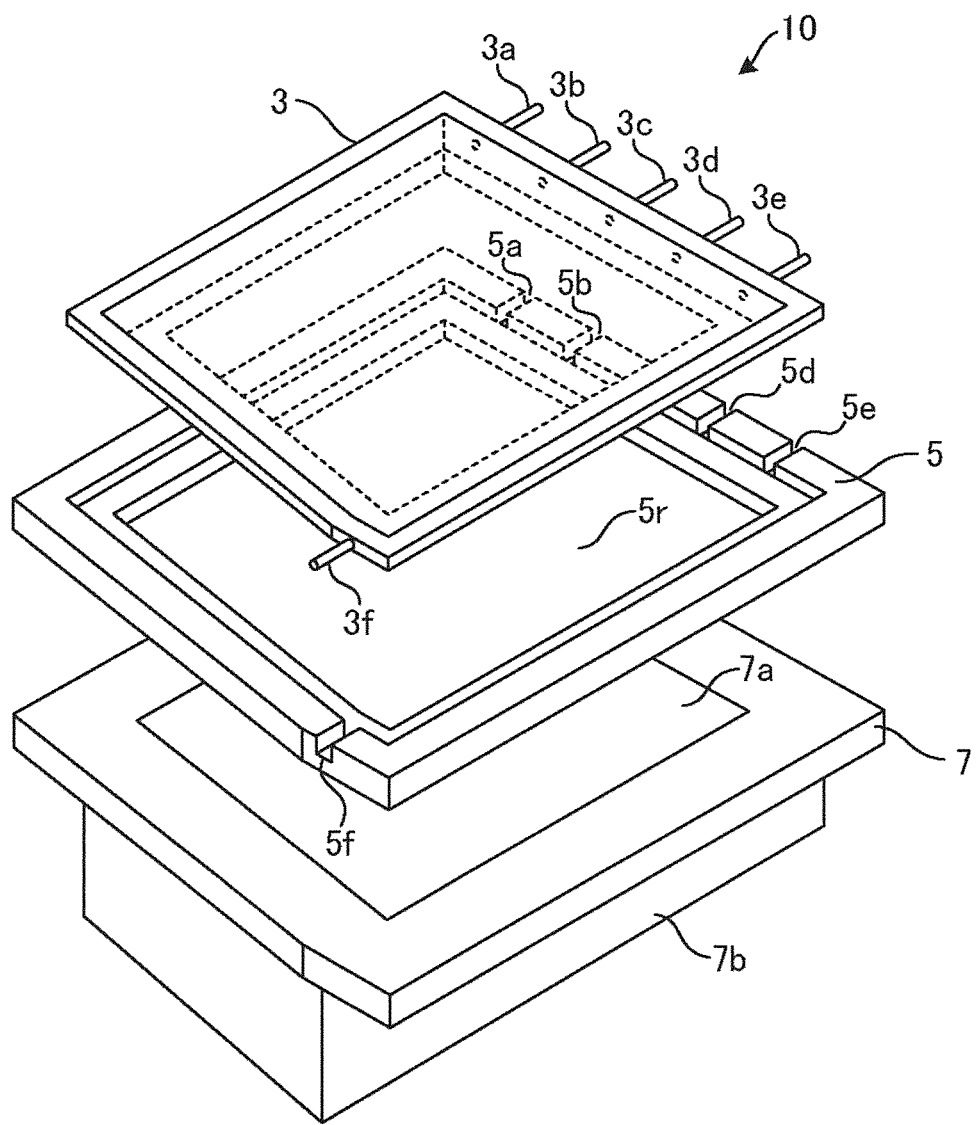
FIG. 1 An exploded perspective view showing a culture device according to a first embodiment of the present invention.

Referring to FIG. 1, the culture device 10 will be described. The culture vessel 3 has a thin internal space while the temperature regulating unit 5 is provided with a concave 5r, where the lower part of the culture vessel 3 is housed in the concave 5r of the temperature regulating unit 5. The culture vessel 3, the temperature regulating unit 5 and the magnetic force regulating unit 7 form a stacking structure. The temperature regulating unit 5 and/or the magnetic force regulating unit 7 may be provided on both or either upper or lower side of the culture vessel 3.

The culture vessel 3 may take a form of a thin layer with a thickness of preferably, but not limited to, 1.0 to 10 mm and more preferably 3.0 to 5 mm. Preferably, but without limitation, the shape of the culture vessel 3 is a rectangle with sides of 20 cm, the material of the culture vessel 3 is a thin transparent flexible resin, and the volume of the culture vessel 3 is 20 to 40 ml. The shape of the culture vessel 3 may be a cube, a cylinder, a prism or a meandering pipe.

The culture vessel 3 is provided with inlet ports 3a-3e and an outlet port 3f so that magnetic particles, a culture solution, carbon dioxide or the like can be supplied to or discharged from the culture vessel 3. Preferably, but without limitation, the inlet ports 3a-3e are provided on one side of the culture vessel 3 while the outlet port 3f is provided on the other side of the culture vessel 3 as shown in FIG. 1.

Preferably, but without limitation, the temperature regulating unit 5 is a temperature managing device such as a thermal cycler, a film heater (sheet heating element) or a coolable and heatable Peltier element. Once the culture vessel 3 is housed in the concave 5r of the temperature regulating unit 5, the surface of the concave 5r will be in close contact with the culture vessel 3, allowing heat exchange between the culture vessel 3 and the temperature regulating unit 5. In the temperature regulating unit 5, recessed port housings 5a to 5f are formed to house the inlet ports 3a-3e and the outlet port 3f. The temperature regulating unit 5 may have any size and any shape as long as the temperature of the culture vessel can be managed promptly. A temperature sensor for detecting the temperature of the culture vessel 3 may also be provided.

The magnetic force regulating unit 7 is provided with a magnet 7a for applying magnetic force from outside to inside the culture vessel 3, and a magnet transferring mechanism 7b that allows the magnet 7a to be brought closer to the culture vessel 3, the magnet 7a to be separated from the culture vessel 3 or the magnet 7a to be vibrated. The movements of the magnet transferring mechanism 7b are controlled by a controller 20 described below. Although the magnet 7a is preferably a permanent magnet or an electromagnet, it is not limited thereto and the magnet 7a may have any size and shape as long as it is capable of applying magnetic field to the magnetic particles. The magnet 7a may be a plurality of magnets 207a arranged in a matrix as in the second embodiment. Instead of the magnet 7a and the magnet transferring mechanism 7b, an electromagnet and a current supply device for supplying and interrupting current to the electromagnet may be provided.

The shape of the magnetic particles contained in the culture solution includes a ball-shape, granules and microparticles regardless of how large or small the diameter is but is not limited to a sphere and may include any shape. The material used for the magnetic particles is preferably, but not limited to, a magnet attracting material free of an eluted substance that has an adverse effect on the cells, for example, ferric oxide such as $Fe_3O_4$, or a nickel-cobalt alloy. When the cultured cells are difficult to directly attach to the magnetic particles, a carrier that can retain the magnetic particles and the cultured cells on its surface can be used. By using the carrier, the cells can indirectly attach to the magnetic particles via the carrier. Examples of the carrier for attaching the cells with the magnetic particles include a fiber assembly, a porous solid material and an ion-exchange resin. The magnetic particles enter and integrate within the gap of the fiber assembly or the pores of the porous solid material while the cells are adsorbed onto the surface of the fiber assembly or the porous solid material. As a preferable carrier, a cellulose carrier can be used. Moreover, such a carrier can also attach cell nutrients on its surface.

A culture system 100 according to the first embodiment of the present invention will be described with reference to FIG. 2. The culture system 100 comprises the culture device 10 shown in FIG. 1, a gas supplying section 8 connected to a gas supplying unit (not shown), a plurality of solution supplying sections 9 for supplying various solutions and a reagent to the culture vessel 3, a magnetic particle separating unit 15 for separating the magnetic particles from the solution containing the cells cultured in the culture vessel 3, a cell sorting port 17 for sorting the cells from the solution containing the cells supplied from the magnetic particle separating unit 15, and a waste liquid bottle 19 for collecting the solution discharged from the cell sorting port 17.

The solution supplying sections 9 supply magnetic particles, various solutions such as a culture solution, a wash fluid, an eluent or the like, a reagent or cells to the culture vessel 3. Although four solution supplying sections are shown in FIG. 2, the number thereof is not limited to four and the number can appropriately be adjusted according to the required reagent and the like. One gas supplying section 8 and four solution supplying sections 9 are connected to the five inlet ports 3a-3e of the culture vessel 3 via flexible connecting tubes (pipelines), respectively. Each of these five connecting tubes is provided with a valve 11. The outlet port 3f of the culture vessel 3 is connected to the magnetic particle separating unit 15 via a flexible connecting tube which is provided with an openable and closable valve 13. The valves 11 and 13 may be valves that can be manually opened or closed with pinchcocks or the like, or solenoid valves, air operated valves or the like that can automatically be opened or closed with the controller 20 described below.

Figure 2:
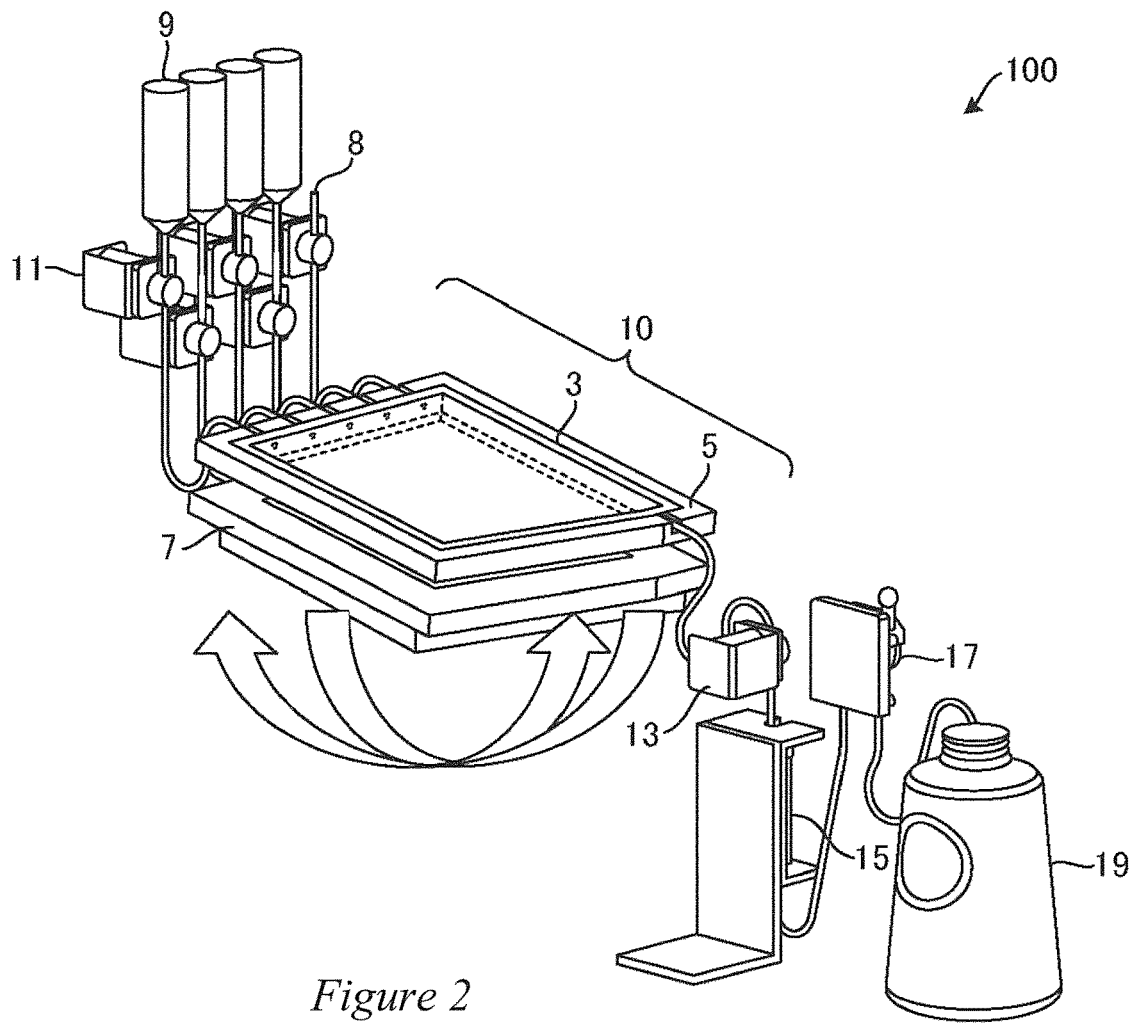
FIG. 2 A perspective view showing a culture system provided with the culture device of FIG. 1.

As shown in FIG. 2, since the solution supplying sections 9 are disposed above the culture vessel 3, the culture solution, the reagent and the like supplied from the solution supplying sections 9 will fall into the culture vessel 3 via the connecting tubes. Alternatively, the various solutions may be pressured with a pump or the like (not shown) for automatic transfer.

The gas supplying section 8 supplies gas with a carbon dioxide concentration and a humidity required for cell culture from the gas supplying unit to the culture vessel. In general, gas conditions with a carbon dioxide concentration of 5%, a humidity of 95%, and a temperature of 37° C. are appropriate for cell culture. Other than providing gas under the above-described conditions into the culture vessel, the gas supplying unit also provides gas with a carbon dioxide concentration, a humidity and a temperature suitably regulated according to the types of the cultured cells and the culture circumstance to the gas supplying section.

The valve 13 is closed during cell culture so that the solution does not leak from the culture vessel 3. At the end of the cell culture, the valve 13 is opened to transfer the solution containing the magnetic particles attached to the cultured cells to the magnetic particle separating unit 15.

The magnetic particle separating unit 15 comprises a second magnetic force regulating unit, which is provided with a separating vessel (not shown), a magnet disposed outside the separating vessel, and a magnet transferring mechanism for transferring said magnet. Once the solution flows into the separating vessel, the magnet approaches the separating vessel to trap the magnetic particles in the solution. Then, only the culture solution is discharged from the separating vessel while retaining the magnetic particles attached to the cultured cells within the separating vessel, thereby separating the magnetic particles from the culture solution in the separating vessel. Thereafter, the cultured cells attached to the magnetic particles are washed and eluted with the wash fluid and the eluent supplied from the solution supplying sections 9 or a solution inlet (not shown) provided in the magnetic particle separating unit 15. The movements of the second magnet transferring mechanism are controlled with the controller 20.

A method for eluting the cells in the separating vessel of the magnetic particle separating unit 15 is preferably, but not limited to, a method including trypsin treatment or a method including exfoliating with a large amount of buffer. According to the present invention, since the cells are transferred into the separating vessel of the magnetic particle separating unit 15 without being attached to the culture vessel 3, the concentration of trypsin used for the cells in the separating vessel can be lowered as compared to the conventional case, placing less stress on the cells.

At the cell sorting port 17, the cultured cells eluted from the magnetic particle separating unit 15 can be sorted and transferred into other vessel while keeping the sterile state. The cell sorting port 17 is provided with a three-way cock (three-way valve) (not shown). After transferring the solution of the wash fluid into the waste liquid bottle 19, the three-way cock can be handled to change the flow so that the solution containing the cultured cells separated from the magnetic particles with the eluent flows to the cell sorting port 17. The cell sorting port 17 is connected to a vessel for receiving the cultured cells. Furthermore, besides the three-way cock, the cell sorting port 17 may be provided with any other mechanism as long as it can change the flow of the solution, for example, a three-way selector ball valve. In FIG. 2, the cell sorting port 17 is shown to be disposed at a position higher than the magnetic particle separating unit 15, the cell sorting port 17 may be positioned lower than the magnetic particle separating unit 15 so that the solution can fall from the magnetic particle separating unit 15 into the cell sorting port 17.

The waste liquid bottle 19 collects the solution discharged from the cell sorting port 17. The end of the waste liquid bottle may be provided with a valve. This valve can be closed so that the bottle can be exchanged while keeping the sterile state.

Figure 3:
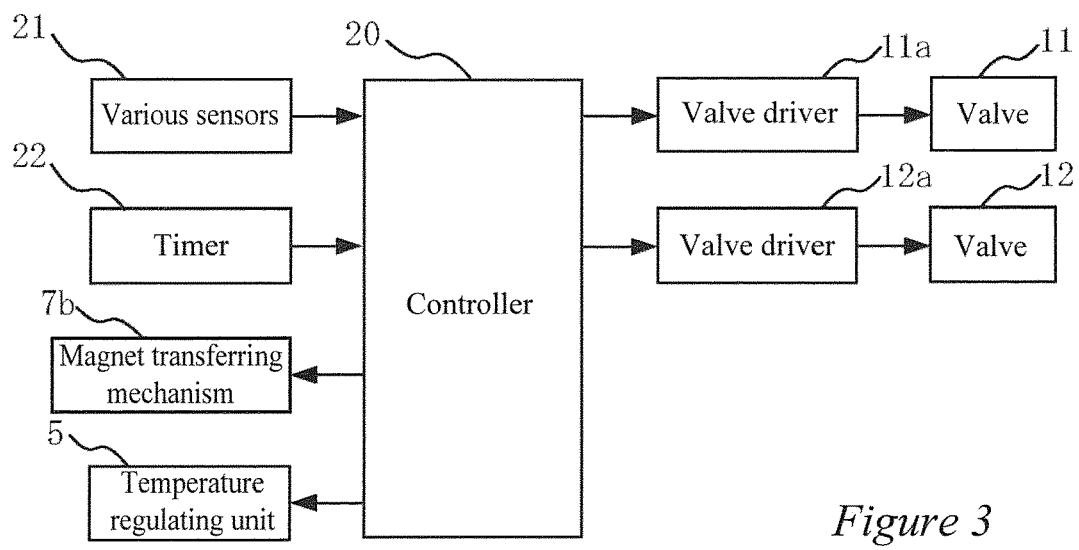
FIG. 3 A block diagram of the culture system of FIG. 2.

FIG. 3 is a block diagram for controlling the culture system 100. The controller 20 is connected to various sensors 21, a timer 22, the magnet transferring mechanism 7b, the temperature regulating unit 5, a valve driver 11a for opening and closing the valve 11 and a valve driver 12a for opening and closing the valve 12. The controller 20 can periodically and regularly move the magnet with the magnet transferring mechanism 7b based on signals from the various sensors 21 according to the input program. Moreover, the controller 20 controls the temperature with the temperature regulating unit 5, opens and closes the valve 11 with the valve driver 11a and opens and closes the valve 12 with the valve driver 12a.

The various sensors 21 may be a temperature sensor, a humidity sensor, a carbon dioxide concentration sensor, a pH sensor, a solution velocity sensor, a solution volume sensor, a bacteria sensor or the like. The culture device 10 may be provided with one or more of the followings as the various sensors 21: a temperature sensor, a humidity sensor, a carbon dioxide concentration sensor, a solution volume sensor, a pH sensor and a bacteria sensor. The solution supplying sections 9, the magnetic particle separating unit 15, the cell sorting port 17 or the waste liquid bottle 19 may be provided with at least one of a solution volume sensor, a pH sensor and a bacteria sensor, as the various sensors 21. The connecting tube in the vicinity of the valve 11 or 12 may be provided with a flow sensor as the sensors 21. The controller 20 can operate and control each component relative to one another or stop them automatically upon detecting abnormality based on the signals from the above-described various sensors 21.

Hereinafter, a method for culturing cells and recovering the cultured cells using the culture system 100 according to the first embodiment of the present invention will be described specifically.

A culture solution containing magnetic particles, cultured cells and a carrier such as a cellulose carrier is supplied from the solution supplying sections 9 to the culture vessel 3. Then, the gas supplying section 8 supplies gas with a carbon dioxide concentration and a humidity required for cell culture to the culture vessel 3. The gas supplying section 8 supplies the gas to the culture vessel 3 such that the gas conditions are maintained to a carbon dioxide concentration of 5%, a humidity of 95%, a temperature of 37° C. The temperature of the solution in the culture vessel 3 is regulated with the temperature regulating unit 5 disposed beneath the bottom surface of the culture vessel 3.

The magnetic particles directly or indirectly attached to the cultured cells in the culture vessel 3 are condensed and fixed on the inner surface of the culture vessel 3 using the magnet 7a of the magnetic force regulating unit 7 brought close to the culture vessel 3. The cell culture is performed by repeating static culture and shake culture. In order to perform shake culture, the magnetic force regulating mechanism 7b is oscillated as indicated by the arrows in FIG. 2 to alter the magnetic force of the magnet, thereby vibrating the magnetic particles in the culture vessel 3. Alternatively, a sliding mechanism (not shown) may be used to vibrate the culture vessel 3 from side to side. Since the position of the culture vessel 3 shifts with the sliding mechanism, the connecting tubes connected to the culture vessel 3 are disposed to have extra lengths so that the connection is maintained even when the position of the culture vessel 3 shifts.

Accordingly, the magnetic particles and thus the cells attached to the magnetic particles can be oscillated to move the positions of the cultured cells on the magnetic particles, thereby agitating the surrounding solution. Due to this agitation, a state where the grown cells can always naturally absorb the nutrients can be maintained.

At the end of the cell culture, the magnet 7a is separated from the culture vessel 3 so that the magnetic particles are dispersed from the inner surface of the culture vessel 3. Then, since the magnetic particle separating unit 15 is disposed at a position lower than the culture vessel 3, the closed valve 13 is opened to allow the culture solution containing the magnetic particles to fall by gravity from the culture vessel 3 to the separating vessel of the magnetic particle separating unit 15.

After allowing the solution to flow into the separating vessel, the magnet of the second magnetic force regulating unit is brought close to the separating vessel, by which the magnetic particles in the solution are fixed on the inner surface of the separating vessel while only the culture solution is discharged from the separating vessel, thereby separating the carriers attached to the cultured cells and the magnetic particles from the culture solution. Thereafter, the carriers attached to the cultured cells and the magnetic particles are washed with a wash fluid supplied from the solution supplying sections 9 or the supply inlet provided in the magnetic particle separating unit 15 and then the cultured cells are eluted from the carrier with an eluent supplied to the separating vessel.

The eluted cultured cells are transferred into other vessel via the cell sorting port 17 while maintaining the sterile state. The waste liquid bottle 19 collects the solution resulting from the round of steps.

Second Embodiment

Figure 4:
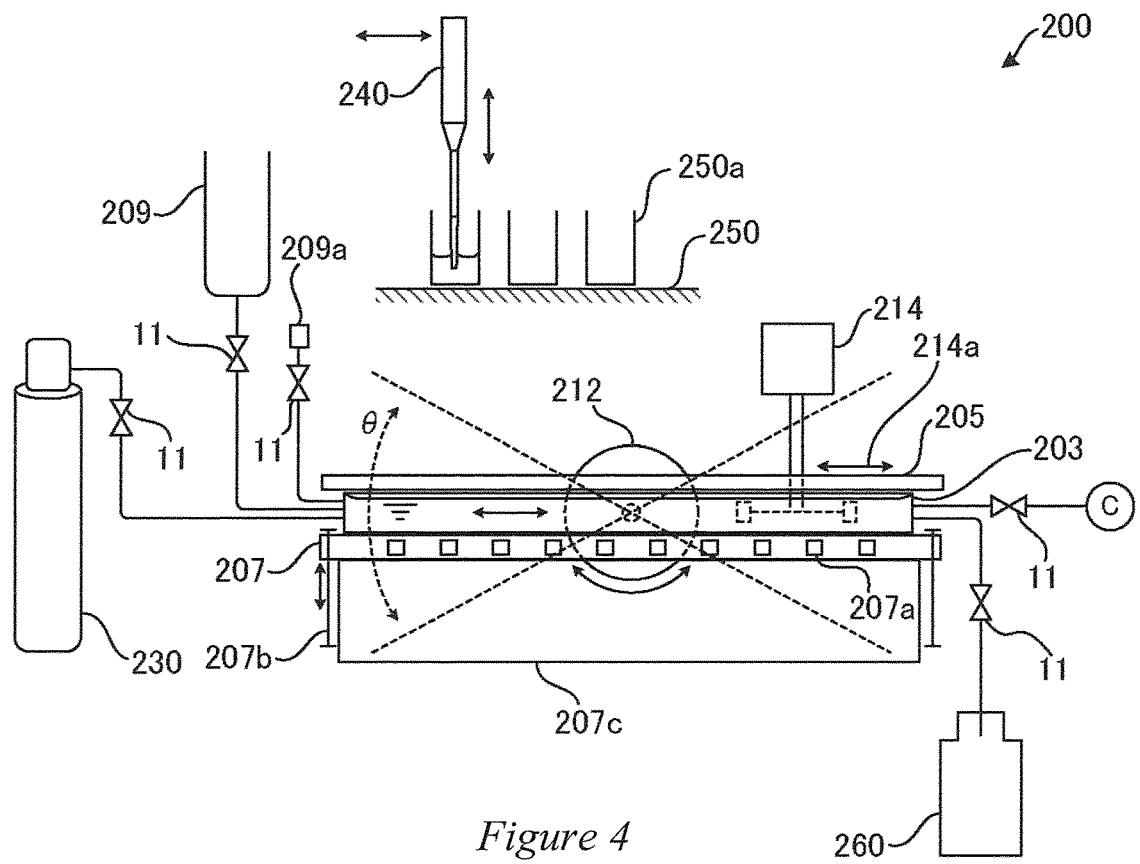
FIG. 4 A schematic side view showing a culture system according to a second embodiment of the present invention.
Figure 5:
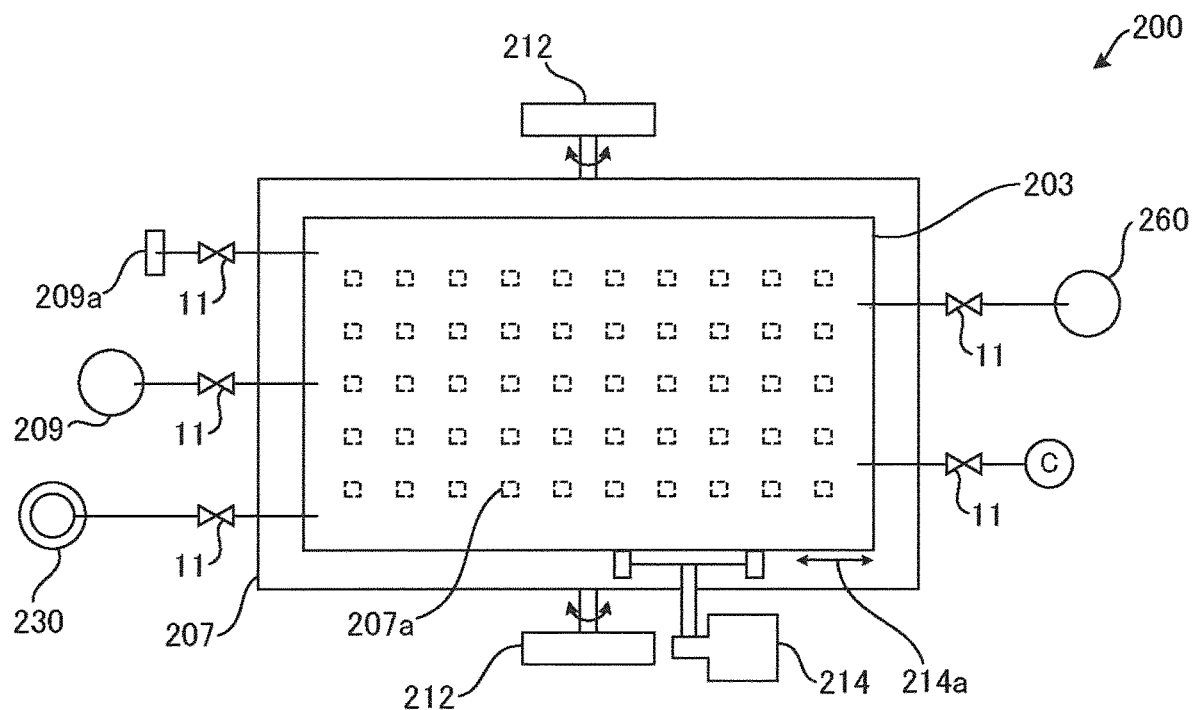
FIG. 5 A schematic top view of the culture system of FIG. 4.

A culture system 200 according to a second embodiment of the present invention will be described with reference to FIGS. 4 to 11. As shown in FIGS. 4 and 5, the culture system 200 is provided with a culture vessel 203 having a thin internal space, a temperature managing unit 205 disposed on the top surface of the culture vessel 203 and a magnetic force regulating unit 207 disposed on the bottom surface of the culture vessel 203. The culture vessel 203 is connected to a tilting mechanism 212 which periodically tilts the culture vessel 203 within an angle range of θ shown in FIG. 4. The tilting mechanism 212 may employ a motor. Preferably, the angle range of the tilting mechanism 212 to tilt the culture vessel 203 may be 10° to 20°.

The culture vessel 203 is connected to a sliding mechanism 214 which periodically slides (vibrates) the culture vessel 203 in the horizontal direction represented by the arrow 214a shown in FIG. 4. The sliding mechanism 214 can be realized by converting the rotation of the motor into a linear motion with a rack or a cam. Since the position of the culture vessel 203 shifts with the tilting mechanism 212 and the sliding mechanism 214, the connecting tubes connected to the culture vessel 203 are disposed to have extra lengths so that the connection is maintained even when the position of the culture vessel 203 shifts.

Although the temperature managing unit 205 is provided on the top surface of the culture vessel 203 in FIG. 4, the temperature managing unit 205 may be provided on both top and bottom surfaces or on the bottom surface of the culture vessel 203. The temperature managing unit 205 used may be, but not limited to, a temperature managing device such as a thermal cycler, a Peltier element or a film heater (sheet heating element).

Figure 10:
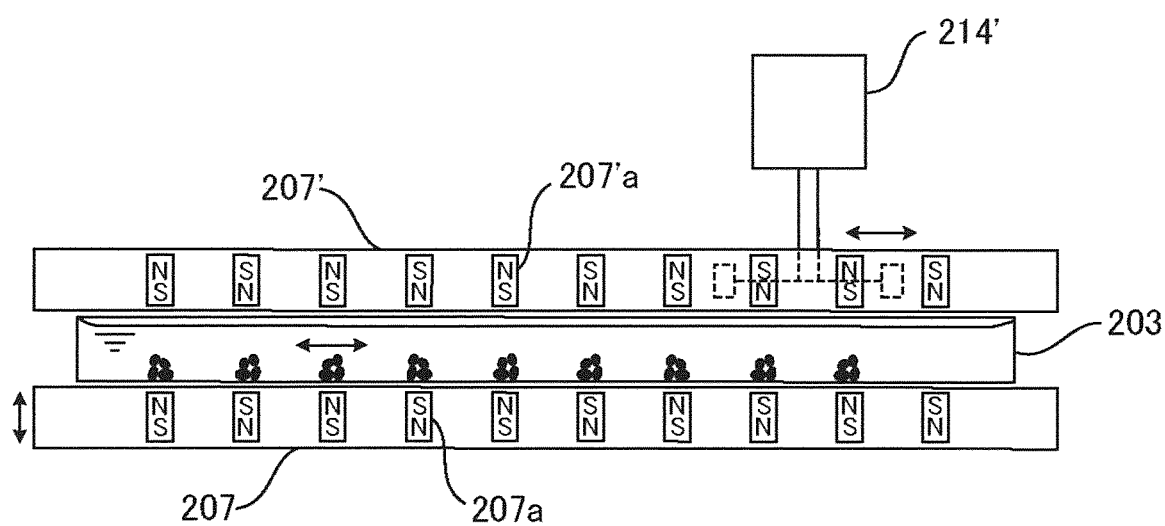
FIG. 10 An enlarged view showing a variation of the culture system of FIG. 4.

The sliding mechanism 214 is not limited to sliding the culture vessel 203 itself as shown in FIG. 4, and it may slide the culture vessel 203 or the magnets 207a relative to one another. For example, as shown in FIG. 10, a sliding mechanism 214' may slide a second magnetic force regulating unit 207' without moving the culture vessel 203. The arrangement of the magnets 207'a in the second magnetic force regulating unit 207' may be the same as the arrangement of the magnets 207a in the magnetic force regulating unit 207. The sliding mechanism 214' may employ the same mechanism as the sliding mechanism 214. In FIG. 10, the second magnetic force regulating unit 207' is disposed on the top surface of the culture vessel 203 and repeatedly slides in the horizontal direction by the sliding mechanism 214'. By this sliding, the magnetic force caused by the magnets 207'a of the second magnetic force regulating unit 207' on the magnetic particles in the culture vessel 203 alters so that the magnetic particles and the cells condensed and fix in the culture vessel 203 are oscillated in the sliding direction (generally horizontal direction). Here, although the temperature managing unit 205 is not shown in FIG. 10, the temperature managing unit may be placed between the culture vessel 203 and the second magnetic force regulating unit 207', or on the top surface of the second magnetic force regulating unit 207'.

In FIGS. 4 and 5, a gas cylinder 230 containing carbon dioxide and the like, a solution supply vessel 209 and an opening 209a are connected to the left side of the culture vessel 203 via flexible connecting tubes having valves 11. The connecting tubes are provided with the valves 11. Since the solution supply vessel 209 is disposed at a position higher than the culture vessel 203, the solution supplied from the solution supply vessel 209 will transfer into the culture vessel 203 by gravity fall.

As shown in FIG. 4, the culture system 200 is provided with an automatic dispenser 240 that can move in three dimensions and a plurality of various vessels 250a for accommodating a reagent, a solution, cultured cells and the like are disposed on a preparation stage 250, so that the automatic dispenser 240 can take up the reagent, the solution, the cultured cells and the like for necessary amounts from the various vessels 250a for preparation and move to the solution supply vessel 209.

In FIGS. 4 and 5, a waste liquid tank 260 for collecting waste liquid from the culture vessel 203 and a connecting point C are connected to the right side of the culture vessel 203 via flexible connecting tubes having valves 11. To the connecting point C, a magnetic particle separating unit 206 shown in FIG. 11 or a magnetic particle separating unit 206' shown in FIG. 12 is connected.

As shown in FIG. 5, the magnetic force regulating unit 207 have a plurality of permanent magnets 207a arranged in a matrix, i.e., equally spaced in horizontal and vertical directions. Each of the permanent magnets 207a included in this array can condense and fix the magnetic particles and the cells contained in the culture solution in the culture vessel 203 on the inner surface of the culture vessel 203. The polarities of the adjacently arranged magnets 207a are constantly opposite to each other. By doing so, the polarities of the magnetic particles attracted by the adjacent magnets 207a will differ from each other and thus repulsive force will result between them. As a result, the magnetic particles and the cells attracted by the magnets 207a are more likely to aggregate to form an agglomerate.

As shown in FIG. 4, the magnetic force regulating unit 207 can approach or separate from the culture vessel 203 along a guide 207b by a magnetic force regulating unit transferring mechanism 207c. When the magnetic force regulating unit 207 approaches the bottom surface of the culture vessel 3, the magnetic force of the magnets 207a can condense and fix (adsorb) the magnetic particles and the cells contained in the culture solution in the culture vessel 203 on the inner bottom surface of the culture vessel 203. Once the magnetic force regulating unit 207 separates from the bottom surface of the culture vessel 3, the magnetic force of the magnets 207a no longer has influence on the culture vessel 203 and thus the magnetic particles and the cells move from the inner bottom surface of the culture vessel 203 and disperse.

Figure 6:
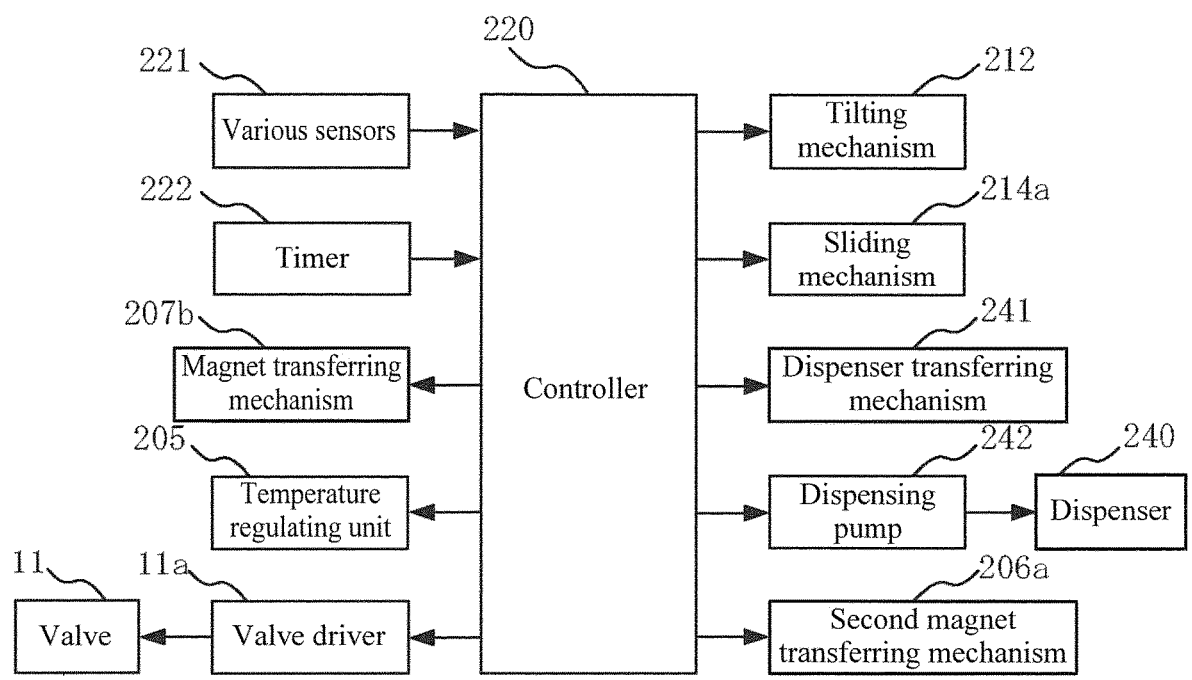
FIG. 6 A block diagram of the culture system of FIG. 4.

FIG. 6 is a block diagram showing control of the culture system 200. To a controller 220, various sensors 221, a timer 222, a magnet transferring mechanism 207b, a temperature regulating unit 205, a valve driver 11a for opening and closing a valve 11, a tilting mechanism 212 for tilting the culture vessel 203, a sliding mechanism 214a for sliding the culture vessel 203, a dispenser transferring mechanism 241 for transferring the dispenser 240 in three dimensions, a dispensing pump 242 for controlling take up and discharge of the automatic dispenser 240 and a second magnet transferring mechanism 206a. The controller 220 uses the automatic dispenser 240 to prepare a solution and the like, dispenses the solution into the solution supply vessel 209, operates the magnet transferring mechanism 207b according to signals from the various sensors 221, controls the temperature with the temperature regulating unit 205, and opens and closes the valve 11 with the valve driver 11a. The controller 220 operates the tilting mechanism 212 and the sliding mechanism 214a to conduct tilting and sliding of the culture vessel 203. The controller 220 controls the transfer of the second magnet transferring mechanism 206a to condense and fix the magnetic particles in the magnetic particle separating unit 206.

The various sensors 221 are a temperature sensor, a humidity sensor, a carbon dioxide concentration sensor, a pH sensor, a solution velocity sensor, a solution volume sensor, a time sensor, a bacteria sensor and the like. The culture vessel 203 may be provided with one or more of the followings as the various sensors 221: a temperature sensor, a humidity sensor, a carbon dioxide concentration sensor, a solution volume sensor, a pH sensor and a bacteria sensor. The solution supply vessel 209, the magnetic particle separating unit 206, the cell recovery vessel 218 or the waste liquid tank 206 may be provided with at least one of the followings as the various sensors 221: a solution volume sensor, a pH sensor and a bacteria sensor. The connecting tube in the vicinity of the valve 11 may be provided with a flow sensor as the sensors 221. The controller 220 can operate and control each component relative to one another or stop them automatically upon detecting abnormality according to signals from the above-described various sensors 221.

Figure 7:
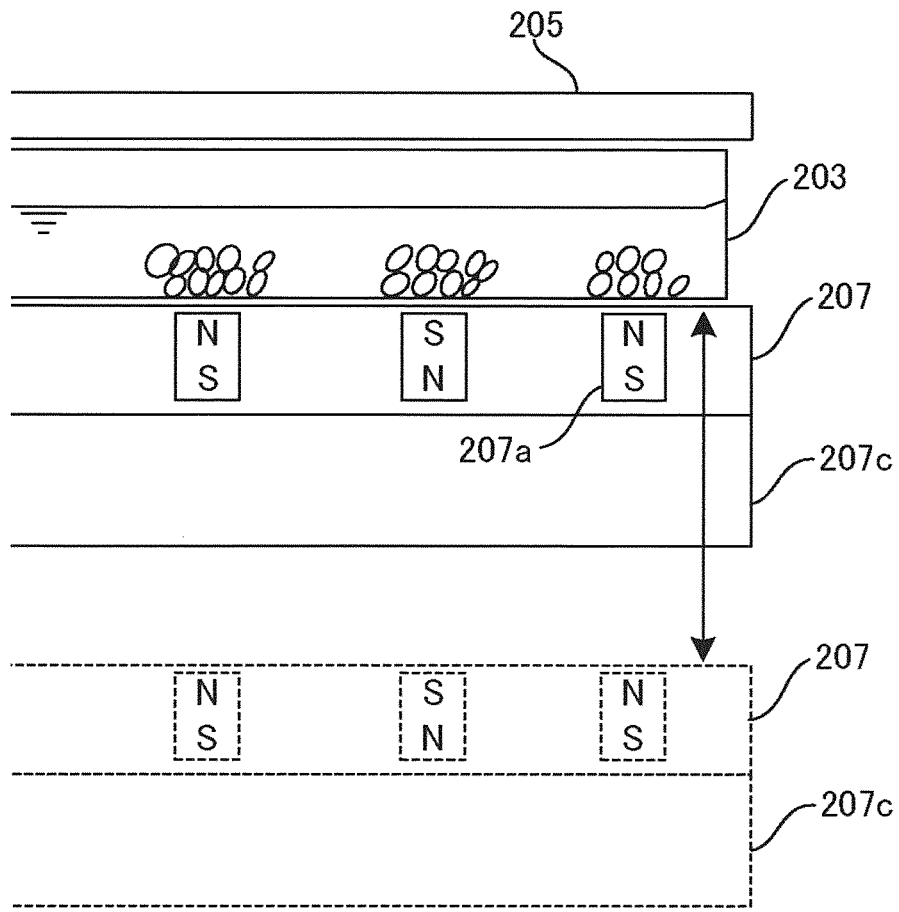
FIG. 7 An enlarged view showing a movement of a magnetic force regulating unit of the culture system of FIG. 4.

As shown in FIG. 7, the culture vessel 203 and the magnetic force regulating unit 207 may be transferred relative to each other in the vertical direction for several to several-tens of millimeters by a separating mechanism 207c. The vertical transfer of the separating mechanism 207c can ensure the control of placing or interrupting the magnetic force of the magnets 207a of the magnetic force regulating unit 207 on the culture vessel 203.

Figure 8:
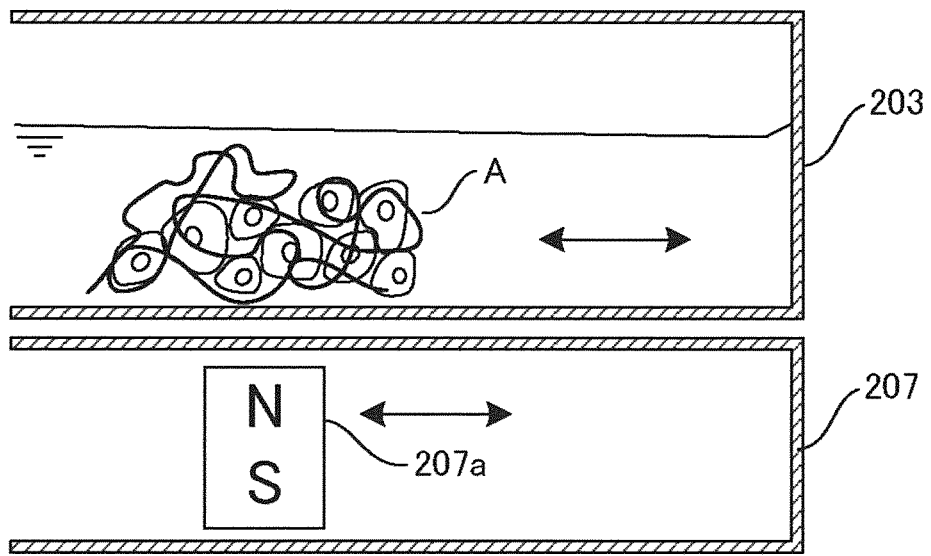
FIG. 8 An enlarged view showing a sliding state in the culture system of FIG. 4.

FIG. 8 shows a state where an agglomerate A (bound body) including the magnetic particles is condensed (aggregated) and fixed on the inner bottom surface of the culture vessel 203 by the magnets 207a. In this state, the sliding mechanism 214 repeatedly slides the culture vessel 203 and the magnets 207a relative to each other for a distance of several to several-tens of millimeters in the horizontal direction represented by the arrows. By doing so, the periphery around the agglomerate A is agitated, by which nutrients can be introduced between the cells included in the agglomerate A. The agglomerate A consists of the magnetic particles, the cultured cells and the filamentous cellulose carrier (carrier).

Figure 9:
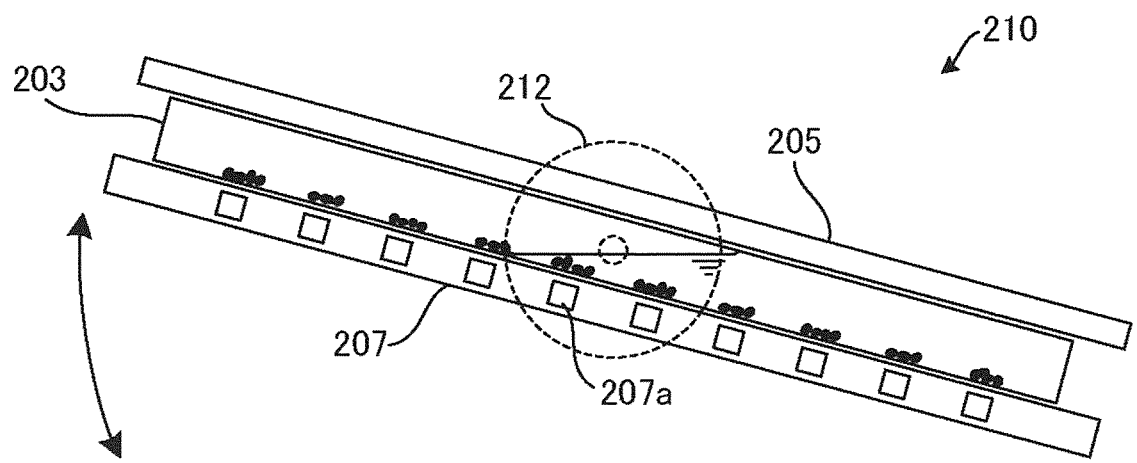
FIG. 9 An enlarged view showing a movement of a tilting mechanism in the culture system of FIG. 4.

As shown in FIG. 9, the tilting mechanism 212 can oscillate a culture device 210 comprising the temperature regulating unit 20, the culture vessel 203 and the magnetic force regulating unit 207 in an angle range of θ. Accordingly, the culture solution can continuously be agitated to supply nutrients to the cells.

Figure 11:
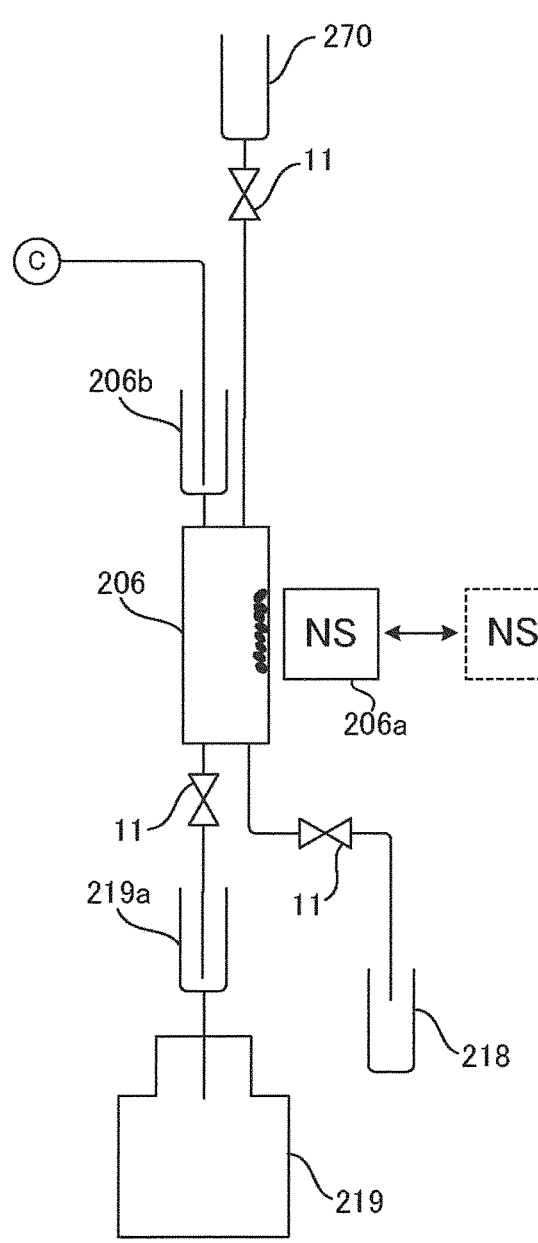
FIG. 11 A schematic view showing a magnetic particle separating unit of the culture system of FIG. 4.
Figure 12:
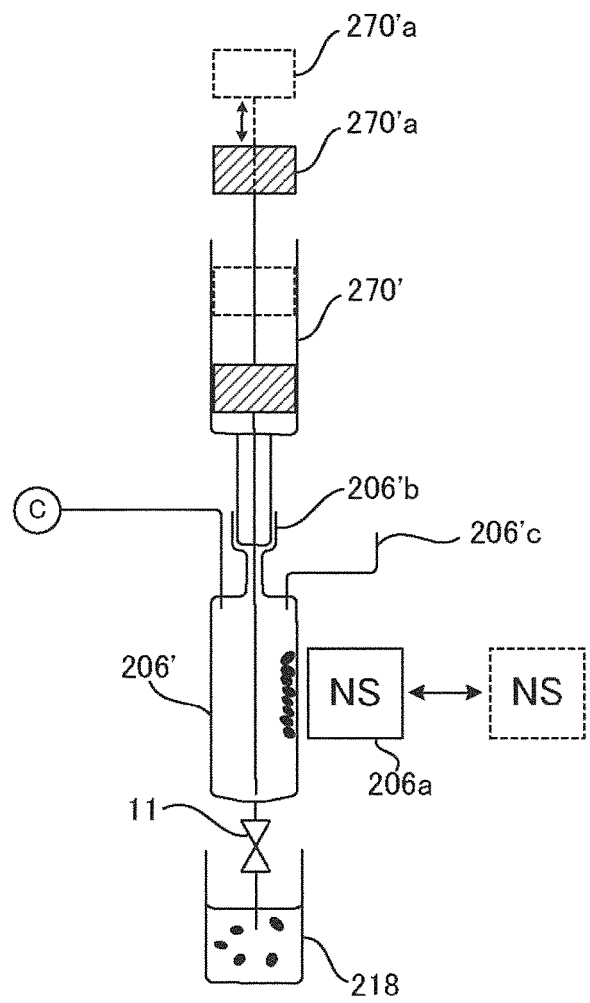
FIG. 12 A schematic view showing a variation of the magnetic particle separating unit of the culture system of FIG. 4.

As shown in FIG. 11, the upper part of the magnetic particle separating unit 206 is connected to a connecting tube that leads to a connecting point C via a coupler 206b (or a lure). The magnetic particle separating unit 206 is disposed at a position lower than the connecting point C and the culture vessel 203. Therefore, by opening the valve 11 (FIG. 4) provided on the tube connecting the culture vessel 203 and the connecting point C, the solution in the culture vessel 203 automatically falls from the culture vessel 203 into the magnetic particle separating unit 206 by gravity. The magnetic particle separating unit 206 is provided with a second magnet transferring mechanism 206a which adsorbs the magnetic particles contained in the solution.

A wash fluid supplying section 270 is provided above the magnetic particle separating unit 206 via a connecting tube provided with the valve 11. Into the wash fluid supplying section 270, a wash fluid, a trypsin solution or the like is dispensed with the automatic dispenser 240, and the resultant, in turn, falls from the wash fluid supplying section 270 into the separating vessel of the magnetic particle separating unit 206. The lower part of the magnetic particle separating unit 206 is connected to a connecting tube provided with a valve 11 and a waste liquid tank 219 coupled to this connecting tube via a coupler (or a lure) 219a. In addition, a cultured cell recovery vessel 218 is disposed below the magnetic particle separating unit 206 via a connecting tube provided with a valve 11. Although the line (connecting tube) connecting the magnetic particle separating unit 206 with the waste liquid tank 219 and the line connecting the magnetic particle separating unit 206 with the cultured cell recovery vessel 218 are provided independently in FIG. 11, they may share a single line halfway through and branch off from a three-way valve for selectively falling into the waste liquid tank 219 or the cultured cell recovery vessel 218.

A magnetic particle separating unit 206' shown in FIG. 12 is a variation of the magnetic particle separating unit 206' shown in FIG. 11. The upper part of the magnetic particle separating unit 206' is connected to a connecting tube that leads to a connecting point C. The magnetic particle separating unit 206 is disposed at a position lower than the connecting point C and the culture vessel 203. The upper part of the magnetic particle separating unit 206' is connected to a cylinder 270' via a coupler 206'b, such that the cylinder 270' is detachable from the magnetic particle separating unit 206'. The cylinder 270' accommodates a piston 270'a that can freely move up and down. By pulling up the piston 270'a from the position indicated by the solid line to the position indicated by the dashed line, the solution in the magnetic particle separating unit 206' can be taken up into the cylinder 270'a. By pushing down the piston 270'a from the position indicated by the dashed line to the position indicated by the solid line, the solution can be discharged from the cylinder 270' into the magnetic particle separating unit 206'. In addition, the upper part of the magnetic particle separating unit 206' is connected to an air vent tube 206'c for admitting or releasing air according to the movement of the piston 270'a.

Hereinafter, a method for culturing a cell and recovering the cultured cells using the culture system 200 according to the second embodiment of the present invention will be described specifically.

A culture solution containing magnetic particles, cultured cells and a carrier such as a cellulose carrier is dispensed into the solution supply vessel 209 using the dispenser 240. The culture solution falls from the solution supply vessel 209 into the culture vessel 203 via the connecting tube. Carbon dioxide and the like are supplied from the gas cylinder 230 into the culture vessel 203. The temperature of the solution in the culture vessel 203 is regulated with the temperature regulating unit 205.

The magnetic particles directly or indirectly attached to the cultured cells in the culture vessel 203 are arranged in a matrix on the inner surface of the culture vessel 3 by the plurality of magnets 207a of the magnetic force regulating unit 207 that are brought closer to the culture vessel 203, and condensed and fix in that arrangement. In this fixed state, the culture vessel 207 is slid from side to side by the sliding mechanism 214 or tilted by the tilting mechanism 212 so that the magnetic particles and the cells are oscillated. Furthermore, the separating mechanism 207b may be used to allow the magnets 207a to approach or separate from the culture vessel 207. Due to these movements, the ambient atmosphere around the cells is agitated, thereby supplying nutrients to the cells.

At the end of the cell culture, the magnetic force regulating unit 207b is separated from the culture vessel 203, by which the cells and the magnetic particles are dispersed in the culture vessel 203 such that the bound bodies of the magnetic particles and the cells stay in a floating state in the culture vessel 203. In this floating state, the valve 11 on the connecting point C side is opened to allow the solution containing the cells and the magnetic particles to fall into the magnetic particle separating unit 206 shown in FIG. 10 or the magnetic particle separating unit 206' shown in FIG. 11 via the connecting point C.

In the magnetic particle separating unit 206 of FIG. 11, the following steps are performed. The solution containing the bound bodies containing the cells and the magnetic particles that fell from the culture vessel 203 is collected in the magnetic particle separating unit 206. In this collected state, the second magnet transferring mechanism 206a is transferred to the position indicated by the solid line to condense and fix the cells and the magnetic particles on the inner surface of the separating vessel of the magnetic particle separating unit 206a. In this fixed state, the valve 11 on the waste liquid tank 219 side is opened so that the solution (culture solution) is separated from the bound body of the magnetic particles and the cells and discharged into the waste liquid tank 219. In the state where the solution has been discharged, the valve 11 on the wash fluid supplying section 270 side is closed to dispense the wash fluid into the wash fluid supplying section 270 using an automatic dispenser 240. In the state where the wash fluid is placed in the wash fluid supplying section 270, the valve 11 on the waste liquid tank 219 side is closed while the valve on the wash fluid supplying section 270 side is opened so that the wash fluid falls into the separating vessel of the magnetic particle separating unit 206. In the state where the wash fluid is placed in the separating vessel, the second magnet transferring mechanism 206a is transferred to the position indicated by the dashed line, whereby the bound bodies of the cells and the magnetic particles are dispersed and thus can be washed in the separating vessel. After washing, the second magnet transferring mechanism 206a is again transferred to the position indicated by the solid line, whereby the bound bodies can be condensed and refix on the inner surface of the separating vessel of the magnetic particle separating unit 206.

In this refixed state, the valve 11 on the waste liquid tank 219 side is opened to separate the wash fluid from the bound bodies and discharge it into the waste liquid tank 219. After discharging the wash fluid, the valve 11 on the waste liquid tank 219 side is closed to allow a separator liquid such as a trypsin solution dispensed with the automatic dispenser 240 to fall into the magnetic particle separating unit 206 via the wash fluid supplying section 270. In the state where the separator liquid is placed in the separating vessel of the magnetic particle separating unit 206, the second magnet transferring mechanism 206a is transferred to the position indicated by the dashed line, by which the bound bodies of the cells and the magnetic particles float in the separating vessel. Furthermore, an agitator such as a vortex mixer (not shown) is used to form a vortex to cause agitation in the separating vessel, by which the bound bodies are disrupted and the magnetic particles are separated from the cells. In this separated state, the second magnet transferring mechanism 206a is transferred to the position indicated by the solid line so that while the magnetic particles are condensed and fixed on the inner surface of the separating vessel, the cells float in the solution in the separating vessel. In this state where the cells are floating, the valve 11 on the cell recovery vessel 218 side is opened to allow the solution containing the cells separated from the magnetic particles to fall into the cell recovery vessel 218, thereby sorting the cultured cells.

The magnetic particle separating unit 206' shown in FIG. 12 performs the following steps instead of the steps performed by the magnetic particle separating unit 206 shown in FIG. 11. The solution containing the bound bodies of the cells and the magnetic particles that fell from the culture vessel 203 is collected by the magnetic particle separating unit 206'. In this collected state, the second magnet transferring mechanism 206a is transferred to the position indicated by the solid line to condense and fix the bound bodies of the cells and the magnetic particles on the inner surface of the separating vessel of the magnetic particle separating unit 206'. In this fixed state, the piston 270a of the cylinder 270' is pulled up to separate the solution (culture solution) from the bound bodies so that the solution is taken up by the cylinder 270'. In the state where the solution has been taken up, the cylinder 270' is removed from the magnetic particle separating unit 206' to discharge the solution from the cylinder 270' into the waste liquid tank (not shown). After washing the cylinder 270', the cylinder 270' that has taken up the wash fluid is connected to the magnetic particle separating unit 206'. In this connected state, the piston 270' is pushed down to charge the wash fluid from the cylinder 270' into the separating vessel of the magnetic particle separating unit 206'. In the state where the wash fluid has been charged into the separating vessel, the second magnet transferring mechanism 206a is transferred to the position indicated by the dashed line to disperse the bound bodies of the cells and the magnetic particles in the separating vessel. In this dispersed state, the bound bodies are washed. At the end of the washing, the second magnet transferring mechanism 206a is again transferred to the position indicated by the solid line so that the bound bodies can be condensed and refixed on the inner surface of the separating vessel of the magnetic particle separating unit 206. In the refixed state, only the wash fluid is taken up by the cylinder 270', which is removed from the magnetic particle separating unit 206' to discharge the wash fluid from the cylinder 270' into the waste liquid tank.

After discharging the wash fluid, the cylinder 270' is washed, and the separator liquid such as a trypsin solution is taken up by the cylinder 270'. This cylinder 270' is connected to the magnetic particle separating unit 206' to charge the separator liquid into the magnetic particle separating unit 206'. In the state where the separator liquid is placed in the vessel of the magnetic particle separating unit 206, the second magnet transferring mechanism 206a is transferred to the position indicated by the dashed line so that the bound bodies of the cells and the magnetic particles float in the separating vessel. Using the cylinder 270', the solution containing the floating bound bodies is repeatedly taken up and discharged so that the bound bodies are disrupted and the cells are separated from the magnetic particles. In this separated state, the second magnet transferring mechanism 206a is transferred to the position indicated by the solid line, the magnetic particles are condensed and fixed on the inner surface of the separating vessel while the cells float in the solution in the separating vessel. In this cell floating state, the valve 11 on the cell recovery vessel 218 side is opened so that the solution containing the cells separated from the magnetic particles falls into the cell recovery vessel 218, thereby sorting the cultured cells.

According to the second embodiment, introduction of cells into the culture system 200 through recovery of the cells can be performed continuously and repeatedly owing to: the gravitational solution transfer; the control of gas supply into the culture vessel 203 with the gas cylinder 230; the opening and closing of the valves 11 with, for example, pinchcocks; and the separation of the cultured cells from the liquid and from the magnetic particles in the cell separating unit 206, 206'. Accordingly, a necessary amount of stem cells such as ES cells and iPS cells can be cultured in an automatic manner so that they can be supplied for individual patient at hospital or the like.

The present invention is feasible for any cells that require culture, including ES cells, iPS cells, somatic stem cells, immune cells, dendritic cells and the like. According to the present invention, mixing, agitation, temperature control, reaction, separation, washing, liquid/gas supply, transfer and the like of the components used for cell culture can automatically be performed with a controller according to a program.

Example

The culture device and the culture system of each embodiment of the present invention are based on the premise that the cultured cells can directly or indirectly attach to the magnetic particles. In this example, an experiment was conducted on the attachment of the cultured cells to the magnetic particles, i.e., the above-described premise of the culture device. In the experiment, an ion-exchange resin carrier was used so that the cultured cells can indirectly attach to the magnetic particles. This experiment was conducted in order to confirm that the cultured cells can keep their shapes while bound to the carrier.

Reagents and consumables used for the experiment were as follows:

Cultured cell line: Jurkat cells (human, T-cell Leukemia, ATCC)

Medium: RPMI medium 1640 (Life technologies, 11875-093)

Fetal bovine Serum: Life technologies, 10437-028

Antibiotic: Antibiotic-Antimycotic, 100× (Life technologies, 15240-062)

Phosphate buffered saline (PBS, pH 7.4): Life technologies, 10010023

Cell cryopreservation solution: Cell Banker (LSI Medience, BLC-1)

Carrier: Crushed matter of strongly-basic anion exchange resin (amberlite IRA400J, particle diameter: 45 to 150 µm)

Culture vessel: Petri dish 35φ for floating culture (Sumitomo Bakelite, MS-1135R)

Disposable pipettes: 50 ml, 25 ml and 5 ml

Disposable chip: 1 ml

Instruments used for the experiment were as follows:

$CO_2$ incubator Heracell 150SS (Helaeus, 155SS)

Inverted microscope (Carl Zeiss MicroImaging, Primo Vert)

Electric pipetter (Thermo Scientific S1 Pipet Filler)

Pipetter P1000 (Gilson, P1000)

To 500 ml of RPMI1640, 50 ml of Fetal Bovine Serum followed by 5 ml of Antibiotic-Antimycotic, 100× were added. The resultant was used as a medium, reserved at 4° C. and restored to room temperature upon use. 10 ml of the medium was sorted into a petri dish in a sterile state. A tube of Jurkat preserved by Cell Banker was taken, melted and the total amount of it was added to the petri dish ($1\times10^6$ cells, 1 ml). The resultant was cultured in a $CO_2$ incubator ($CO_2$: 5%) at 37° C. for three days.

9 ml of RPMI1640 was sorted into a new petri dish in a sterile state. The culture solution cultured for three days was agitated with an electric pipetter. 1 ml of the culture solution was added to the petri dish and the culture solution was agitated with the electric pipetter. 200 µl of a carrier (5 g/ml) was added to the petri dish and the culture solution was agitated with the electric pipetter. Agitation with the electric pipetter was conducted by repeating the movements of taking up and discharging the total amount of the culture solution for 10 times. The agitated culture solution was observed with an inverted microscope. The petri dish was cultured in a $CO_2$ incubator ($CO_2$: 5%) for three days and the culture solution was observed with an inverted microscope. Following another three days of culture, the culture solution was observed with the inverted microscope.

Figure 13:
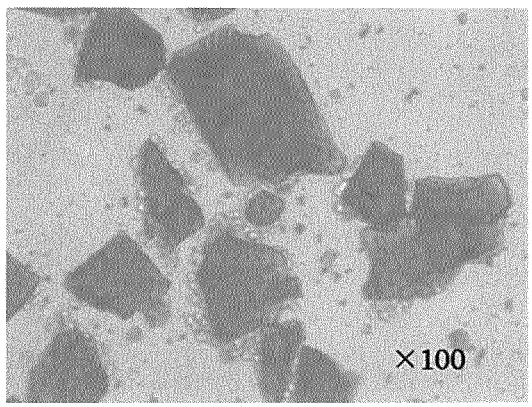
FIG. 13 Pictures showing the results of culture as a test for the premise on which the culture device of the present invention stands.
Figure 13:
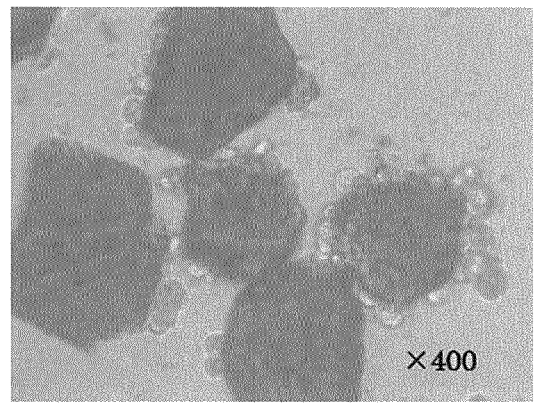
Figure 13:
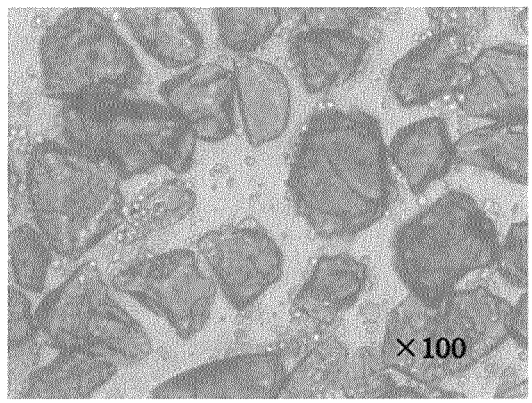
Figure 13:
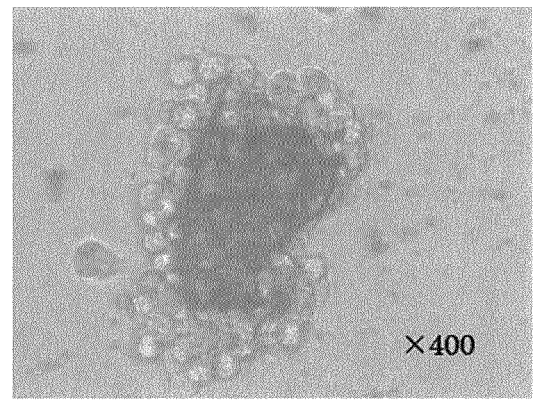
Figure 13:
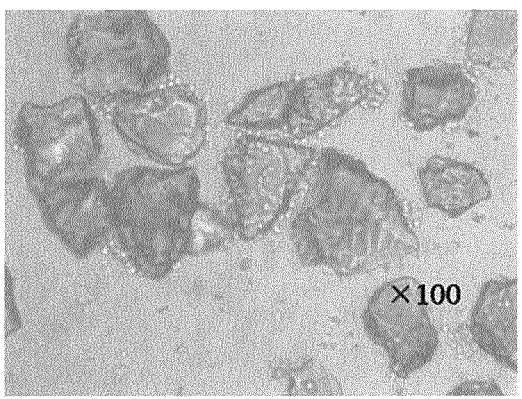
Figure 13:
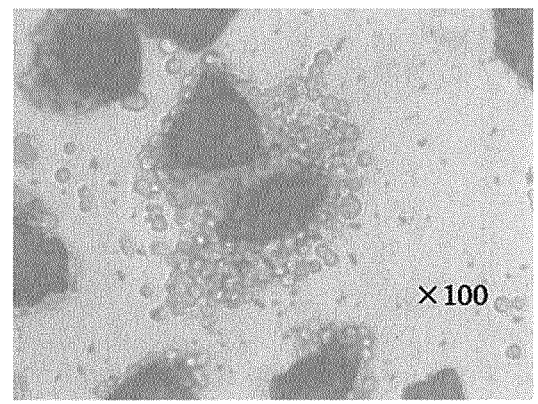

The pictures of the results of observation (Day 0, Day 3 and Day 5) are shown in FIG. 13. "×100" and "×400" in FIG. 13 represent the magnifications of the inverted microscope, respectively. As can be appreciated from FIG. 13(A), the Jurkat cells bound with the carrier immediately after making contact with the carrier. Moreover, as can be appreciated from FIGS. 13(B) and 13(C), the stirred culture appeared to allow the cells to proliferate while maintaining the binding between the cells and the carrier even after three and five days. Therefore, the cells were suggested to be capable of proliferating on the carrier while bound to the carrier in the agitating state.

Although magnetized carrier was not used in the above-described experiment, it is possible to magnetize the carrier while maintaining the state of the surface layer of the carrier. Since a carrier made of an ion-exchange resin binds to magnetic particles made of iron powder, the carrier can indirectly be magnetized by mixing them. Such binding is described, for example, in Japanese Unexamined Patent Application Publication No. 2009-247244, "Method for separating microorganism comprising step of binding carrier and magnetic body" filed by the present Applicant, which is incorporated herein by reference.

DESCRIPTION OF REFERENCE NUMERALS

3 Culture vessel
5 Temperature regulating unit
7 Magnetic force regulating unit
7a Magnet
7b Magnet transferring mechanism
8 Gas supplying section
9 Solution supplying section
10 Culture device
11 Valve
15 Magnetic particle separating unit
17 Cell sorting port
19 Waste liquid bottle
100 Culture system
203 Culture vessel
205 Temperature regulating unit
206 Magnetic particle separating unit
207 Magnetic force regulating unit
207a Magnet
207c Transferring mechanism
214 Sliding mechanism
218 Recovery vessel
230 Gas cylinder
240 Dispenser
260 Waste liquid tank
200 Culture system

The invention claimed is:

1. A culture device, comprising:
a culture vessel in which cells are accommodated and cultured;
magnetic particles that directly or indirectly attach to the cells;
a solution in the culture vessel;
a temperature regulating unit for controlling the temperature of the culture vessel;
a plurality of magnets spaced at intervals disposed outside the culture vessel; and
a magnetic force regulating unit for regulating the magnetic force of the plurality of magnets disposed outside the culture vessel,
wherein the magnetic force regulating unit regulates the magnetic force of the plurality of magnets to conduct cell culture in a state where the magnetic particles and the attached cells are retained to a predetermined region within the culture vessel,
wherein the magnetic force regulating unit comprises a magnet carrier to which the plurality of magnets are fixed, and the magnet carrier is movable along a guide, wherein movement of the magnet carrier along the guide alters a distance between the plurality magnets fixed to the magnet carrier and the culture vessel to regulate the magnetic force of the plurality of magnets disposed outside the culture vessel acting on the magnetic particles within the culture vessel,
wherein the culture vessel, the temperature regulating unit and the magnetic force regulating unit are stacked together into a stacking structure, and the stacking structure is rotationally supported about an axis extending parallel to surfaces of the culture vessel for rotation of the stacking structure about the axis to integrally tilt the culture vessel, the temperature regulating unit and the magnetic force regulating unit together,
wherein the culture vessel has a first side, a second side that is opposite the first side, and a pair of sides between the first side and the second side, a solution supply vessel connects on the first side of the culture vessel via a flexible connecting tube having a valve, and a waste liquid tank connects on the second side of the culture vessel via a flexible connecting tube having a valve, the solution supply vessel is disposed at a positon higher than the culture vessel and the waste liquid tank is disposed at a positon lower than the culture vessel, and the axis is provided on the pair of sides of the culture vessel.

2. The culture device according to claim 1, wherein the magnetic force regulating unit regulates the magnetic force of the plurality of magnets to disperse the magnetic particles and the cells in the culture vessel.

3. The culture device according to claim 1, wherein each of the plurality of magnets is arranged so as to oppose one surface of the culture vessel.

4. The culture device according to claim 1, wherein each of the plurality of magnets is arranged such that the polarity thereof differs from the polarity of the adjacent magnet.

5. The culture device according to claim 1, wherein the plurality of magnets are arranged in a matrix.

6. The culture device according to claim 1, wherein the magnetic particles and the cells are condensed or aggregated in a state where they are retained to the predetermined region in the culture vessel.

7. The culture device according to claim 1, wherein the magnetic force regulating unit brings the plurality of magnets closer to the culture vessel to conduct cell culture in a state where the magnetic particles and the cells are retained to the predetermined region.

8. The culture device according to claim 1, comprising a sliding mechanism for sliding the plurality of magnets and the culture vessel relatively with respect to one another.

9. The culture device according to claim 8, wherein the cell culture is conducted by shake culture with the sliding mechanism.

10. The culture device according to claim 1, comprising an oscillating mechanism for oscillating the culture vessel.

11. The culture device according to claim 1, wherein the magnetic force regulating unit charges the solution into the culture vessel or discharges the solution from the culture vessel in a state where the magnetic particles and the cells are retained to the predetermined region in the culture vessel.

12. The culture device according to claim 1, wherein the magnetic force regulating unit conducts cell culture by combining multiple movements selected from: bringing the plurality of magnets closer; vibrating the plurality of magnets; and separating the plurality of magnets.

13. The culture device according to claim 1, wherein the magnetic force regulating unit collects the solution containing the cultured cells from the culture vessel in a state where the magnetic particles and the cells can be dispersed in the culture vessel.

14. The culture device according to claim 1, wherein at least one of the temperature regulating unit and the magnetic force regulating unit is detachable from the culture vessel.

15. A culture system comprising the culture device according to claim 1, the system comprising a supplying section for supplying a material and a solution used for the cell culture to the culture vessel and a magnetic particle separating unit for separating the magnetic particles from the solution containing the cells cultured in the culture vessel.

16. The culture system according to claim 15, wherein the solution is transferred by gravity fall.

17. The culture system according to claim 15, wherein the supplying section, the culture vessel and the magnetic body separating unit are disposed from top to bottom in this order.

18. The culture system according to claim 15, wherein the supplying section and the culture vessel, and the culture vessel and the magnetic body separating unit are connected via pipelines, respectively.

19. The culture system according to claim 18, comprising valves for opening and closing the respective pipelines.

20. The culture system according to claim 15, comprising a dispensing mechanism for dispensing the material and the solution used for cell culture into the supplying section.

21. A method for culturing a cell, comprising a step of conducting cell culture using the culture device according to claim 1.

22. A method for culturing a cell using the culture system according to claim 15, the method comprising the steps of:
   supplying a material and a solution used for cell culture from the supplying section to the culture vessel;
   culturing cells using the culture device; separating the magnetic particles from the solution containing the cells using the magnetic particle separating unit; and
   sorting out the cells from the solution separated from the magnetic particles.

23. The method according to claim 22, comprising a step of dispensing the material or the solution used for cell culture into the supplying section by using a dispensing mechanism.

24. The method according to claim 22, wherein a controller automatically performs each of the steps.

25. The culture device according to claim 1, further comprising a gas cylinder supplying carbon dioxide to the culture vessel.

* * * * *